United States Patent
Vágó et al.

[11] Patent Number: 5,942,506
[45] Date of Patent: Aug. 24, 1999

[54] 1-[2-(SUBSTITUTED VINYL)]-5H-2,3-BENZODIAZEPINE DERIVATIVES

[75] Inventors: Pál Vágó; József Reiter; István Gyertyán; István Gacsályi; András Bilkei-Gorzó; András Egyed; Ferenc Andrási; Anna Bakonyi; Pál Berzsenyi; Hilda Botka; Tamás Hámori; Cecilia Salamon Haskáné; Edit Horváth; Katalin Horváth; Péter Körösi; Györgyné Máté; Imre Moravcsik; Eszter Szentkuti; Gábor Zólyomi; Gábor Blaskó; Klára Daróczi Kazóne; Gyula Simig; Károly Tihanyi; Judit Bajnógel, all of Budapest, Hungary

[73] Assignee: GIS Gyogyszergyar Rt., Budapest, Hungary

[21] Appl. No.: 08/599,236

[22] Filed: Feb. 9, 1996

[30] Foreign Application Priority Data

Feb. 9, 1995 [HU] Hungary ................................ 9500385
Nov. 24, 1995 [HU] Hungary ................................ 9503353

[51] Int. Cl.$^6$ ................ A61K 31/55; C07D 243/02; C07D 243/04
[52] U.S. Cl. ................ 514/220; 514/221; 540/548; 540/567
[58] Field of Search .................... 540/557, 567, 540/548; 514/220, 221

[56] References Cited

U.S. PATENT DOCUMENTS 4,840,948  6/1989  Lang et al. .................... 514/221

*Primary Examiner*—John M. Ford
*Attorney, Agent, or Firm*—Smith, Gambrell & Russell; Beveridge, DeGrandi, Weilacher & Young Intellectual Property Group

[57] ABSTRACT

This invention relates to new 1-[2-(substituted vinyl)]-5H-2,3-benzodiazepine derivatives, a process for the preparation thereof, pharmaceutical compositions comprising the same, to the use of the said benzodiazepine derivatives for the treatment of diseases and for the preparation of pharmaceutical compositions suitable for the treatment of diseases. The compounds according to the invention correspond to the general formula (I),

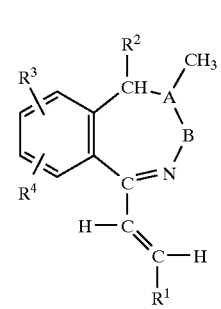

(I)

wherein the variables are herein below defined, and the compounds possess central nervous activities.

12 Claims, No Drawings

1-[2-(SUBSTITUTED VINYL)]-5H-2,3-BENZODIAZEPINE DERIVATIVES

This invention relates to new 1-[2-(substituted vinyl)]-5H-2,3-benzodiazepine derivatives, a process for the preparation thereof, pharmaceutical compositions comprising the same, to the use of the said benzodiazepine derivatives for the treatment of diseases and for the preparation of pharmaceutical compositions suitable for the treatment of diseases.

So far 5H-2,3-benzodiazepine derivatives containing a phenyl, naphtyl, substituted phenyl, furyl, thienyl or hydroxystyryl substituent at the 1 position of the basic molecule skeleton have been described [(Hungarian patent specifications Nos. 155,572, 179,018, 195,788, 191,702 and 206,719; J. Chem. Soc. Perkin I. 1973, 2543; 1980, 1718; 1984, 849; Il Farmaco-Ed. Sc. 40, 942 (1985); Chem. Ber. 107, 3883 (1974)]. A group of the known compounds affects the central nervous system, the 5H-2,3-benzodiazepine derivatives belonging to the other group possess a positive inotropic effect and do not exert any central nervous activity.

The known 2,3-benzodiazepines affecting the central nervous system possess anxiolytic and antiaggressive activities, but—contrary to the traditional 1,4-benzodiazepines—they do not exert a muscle relaxant effect, furthermore the anxiolytic effect is complemented by a neuroleptic activity. The known nerisopam belonging to this group also exerts both anxiolytic and neuroleptic activities, but it has a considerable cataleptic side-effect, too. The aim of the invention was to provide new 2,3-benzodiazepine derivatives comparable to the hitherto known 1,4- and 2,3-benzodiazepines considering the anxiolytic activity, but devoid of any cataleptogenic side-effect hindering the therapeutic application.

Besides, about 20% of the civilized world's population suffer from anxiety, so the treatment of this disease is of high importance. The overwhelming majority of the drugs applied in the therapy of anxiety are 1,4-benzodiazepine derivatives. Said drugs exert, however, some undesirable side-effects, such as sedation, muscle relaxation and somnolence [Patel, J. B. and Malich, J. B.: Neuropharmacological profile of an anxiolytic, in: Anxiolytics: Neurochemical behavioural and clinical perspectives. (Eds.: Malich, J. B., Enna, S. J. and Yamuúamura, H. I., Raven Press, New York 1983, pp. 173–191; File, S. L.: The contribution of behavioural studies to the neuropharmacology of anxiety, Neuropharmacology 1987, 26, 877–866.]

A further aim of the present invention was to provide new 2,3-benzodiazepine derivatives exerting an outstanding anxiolytic effect even at low doses, but contrary to the known anxiolytics—having practically no influence on the movement activity of the animals even at high doses.

It has been found that the compounds according to the invention meet the above requirements.

According to an aspect of the present invention there are provided 1-[2-(substituted vinyl)]-5H-2,3-benzodiazepine derivatives of general formula (I),

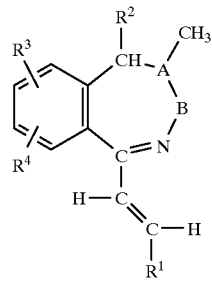

(I)

wherein
A and B together form a group of the formula =C=N— or =CH—NH—;
$R^1$ represents phenyl optionally carrying 2 or 3 hydroxy groups or 1 to 3 identical or different substituent(s) selected from the group consisting of halogen, trifluoromethyl, nitro, cyano, amino, $C_{1-3}$ alkylamino, di-($C_{1-3}$ alkyl)-amino, $C_{1-4}$ alkanoylamino, $C_{1-4}$ alkyl, $C_{1-4}$ alkoxy, carboxy, ($C_{1-4}$ alkoxy)-carbonyl $C_1$–$C_4$ alkoxycarbonyloxy and methylenedioxy; naphtyl optionally carrying a substituent selected from the group consisting of hydroxy, $C_{1-4}$ alkoxy and $C_{1-4}$ acyloxy; furyl, thienyl or indolyl;
$R^2$ stands for hydrogen or $C_{1-4}$ alkyl;
$R^3$ and $R^4$ each represents $C_{1-4}$ alkoxy attached to positions 7 and 8 of the benzodiazepine ring, or
$R^3$ and $R^4$ together form a 7,8- or 8,9-methylenedioxy group,
and pharmaceutically acceptable acid addition salts thereof.

Preferred representatives of the compounds of general formula (I) are those wherein A and B together represent a group of the formula =C=N—, $R^1$ represents phenyl optionally carrying one or two fluoro, cyano, trifluoromethyl, amino, di-($C_{1-3}$ alkyl)-amino or $C_{1-4}$ alkoxy substituent(s), $R^2$ stands for hydrogen and $R^3$ and $R^4$ together form 7,8-methylenedioxy, and pharmaceutically acceptable acid addition salts thereof.

Particularly preferred representatives of the compounds according to the invention are the following
1-(4-dimethylaminostyryl)-4-methyl-7,8-dimethoxy-5H-2,3-benzodiazepine,
1-(4-aminostyryl)-4-methyl-7,8-dimethoxy-5H-2,3-benzodiazepine,
1-(3,4-dimethoxystyryl)-4-methyl-7,8-dimethoxy-5H-2,3-benzodiazepine,
1-(4-fluorostyryl)-4-methyl-7,8-methylenedioxy-5H-2,3-benzodiazepine,
and pharmaceutically acceptable acid addition salts thereof.

The term "lower" used throughout the specification and claims is intended to mean 1 to 4 carbon atom(s). The term "alkyl" refers to straight or branched ones having the given number of carbon atoms, such as methyl, ethyl, n-propyl etc. The term "alkenyl" may include straight or branched ones such as vinyl, 1-methylvinyl, 2-methylvinyl, 1-propenyl, 2-propenyl or the like. The term "alkanoylamino" relates to straight or branched chained aliphatic carboxylic acid amide groups (e.g. acetylamino, propanoylamino etc.). The "alkoxycarbonyl groups" are carboxyl groups esterified by straight or branched chained aliphatic alcohols having 1 to 4 carbon atom(s), such as methoxycarbonyl, ethoxycarbonyl etc. The term "acyloxy group" relates to hydroxy groups acylated by aliphatic carboxylic acids having 1 to 4 carbon atom(s) (e.g. acetoxy, tert.butoxycarbonyloxy etc.,. The term "halogen atom" encompasses all the four halogen atoms, such as fluorine, chlorine, iodine, and bromine.

Pharmaceutically acceptable acid addition salts of the compounds of general formula (I) can be formed with inorganic acids (e.g. hydrohalides, such as hydrochloric acid or hydrobromic acid, sulfuric, phosphoric or perhaloacids, such as perchloric acid), organic carboxylic acids (e.g. fumaric, acetic, propionic, glycolic, maleic, hydroxymaleic, ascorbinic, citric, malic, salicylic, lactic, cinnamic, benzoic, phenylacetic, p-aminobenzoic, p-hydroxybenzoic, p-aminosalicylic acid etc.), alkylsulfonic acids (e.g. methanesulfonic, ethanesulfonic acid), or arylsulfonic acids (e.g. p-toluenesulfonic, p-bromophenylsulfonic, naphtylsulfonic, sulfanilic acid).

According to a further aspect of the present invention there is provided a process for the preparation of 1-[2-(substituted vinyl)]-5H-2,3-benzodiazepine derivatives of general formula (I), wherein A, B, $R^1$, $R^2$, $R^3$ and $R^4$ are as stated above, which comprises a) for the preparation of compounds of general formula (I), wherein A and B together form a group of the formula =C=N—, and $R^1$, $R^2$, $R^3$ and $R^4$ are as stated above, reacting a 2-benzopyrilium perchlorate of general formula (II),

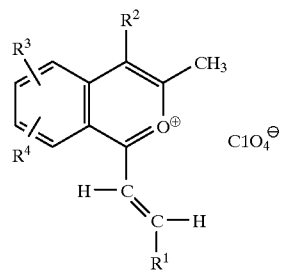

(II)

wherein $R^1$, $R^2$, $R^3$ and $R^4$ are as stated above, with hydrazine hydrate, or b) for the preparation of 1-[2-(substituted vinyl)]-5H-2,3-benzodiazepines of general formula (I), wherein A and B together form a group of the formula =C=N—, $R^3$ and $R^4$ are independently $C_{1-4}$ alkoxy attached to positions 7 and 8 of the benzodiazepine ring, or $R^3$ and $R^4$ together form a 7,8-methylenedioxy group, $R^1$ stands for aminophenyl, ($C_{1-3}$ alkyl)-aminophenyl, di-($C_{1-3}$ alkyl)-aminophenyl or ($C_{1-4}$ alkanoyl)-aminophenyl, which groups optionally carry two hydroxy groups or one or two identical or different substituent(s) selected from the group consisting of halogen, trifluoromethyl, nitro, cyano, amino, methylenedioxy, $C_{1-4}$ alkyl, $C_{1-4}$ alkoxy, carboxy and ($C_{1-4}$alkoxy)-carbony and $R^2$ is as stated above, reducing a compound of general formula (I), wherein $R^1$ stands for nitrophenyl optionally carrying two hydroxy groups or one or two identical or different substituent(s) selected from the group consisting of halogen, trifluoromethyl, nitro, cyano, amino, methylenedioxy, $C_{1-4}$ alkyl, $C_{1-4}$ alkoxy, carboxy and ($C_{1-4}$ alkoxy)-carbonyl $C_1$–$C_4$ alkoxycarbonyloxy, with hydrazine hydrate in the presence of a catalyst, and optionally subjecting the thus-obtained amino compound to acylation or alkylation, or c) for the preparation of compounds of general formula (I), wherein A and B together form a group of the formula =CH—NH—, $R^1$ stands for phenyl carrying a fluoro atom a trifluoro-methyl or a cyano group, $R^2$ represents hydrogen and $R^3$ and $R^4$ together form a 7,8- or 8,9-methylenedioxy group, reducing a compound of general formula (I), wherein A and B together form a group of the formula =C=N— and $R^1$, $R^2$, $R^3$ and $R^4$ are as stated above, with a complex metal hydride and/or a borane complex, and, if desired, converting the base of general formula (I) thus obtained into an acid addition salt thereof.

According to variant a) of the process according to the invention a 2-benzopyrilium perchlorate of general formula (II) is reacted with hydrazine hydrate. The reaction is preferably carried out in a solvent, but it can also be performed without using any solvent, in the excess of the applied hydrazine hydrate. As solvent polar or apolar solvents, preferably water, lower alcohols, dioxane, tetrahydrofurane, dichloromethane, chloroform, dimethylformamide, dimethyl sulfoxide, pyridine or the mixtures thereof may be used. The reaction is carried out at a temperature between 0° C. and the boiling point of the reaction mixture, preferably between +10° C. and +120° C. It is preferable to carry out the reaction with concentrated (90 to 100%) hydrazine hydrate used in an excess of 1 to 3 mole(s).

According to a preferred embodiment of variant a) of the process according to the present invention the 2-benzopyrilium perchlorate of general formula (II) is reacted with 3 molar equivalents of 90–100% hydrazine hydrate in a lower alcohol, preferably ethanol, at room temperature, the crude product is separated from the reaction mixture, the salt-like side-products are dissolved from the desired product in hot water, the latter product is filtered off and optionally either suspended in or recrystallized from a suitable solvent, preferably a lower alcohol.

According to another preferred embodiment of variant a) of the process according to the present invention the compound of general formula (II) is suspended in a solvent and reacted with 3 equivalents of 90–100% hydrazine hydrate first at room temperature for 1–3 hours, then either at a temperature between 45° C. and 50° C. for 10 to 50 minutes or at a temperature between 70° C. and 100 ° C. for half an hour. When the compound of general formula (II) is barely soluble at room temperature or when the compound of general formula (I) begins to separate from the reaction mixture during the reaction, it is preferable to apply an elevated temperature at the end of the reaction.

According to a further preferred embodiment of variant a) of the process according to the invention the compound of general formula (II) is added to a mixture of 3 equivalents of 90–100% hydrazine hydrate and dimethylformamide at a temperature between 10° C. and 15° C., and the reaction mixture is kept at room temperature. The end-product separates from the solution upon adding some water to the mixture. The side-product is then washed out of it with water and the end-product is optionally purified by recrystallization or boiling in an alcohol.

According to variant b) of the process according to the invention a benzodiazepine derivative of general formula (I) carrying an optionally substituted aminophenyl, mono- or di-($C_{1-4}$ lower alkyl)-aminophenyl or $C_{1-4}$ alkanoyl-aminophenyl in the place of $R^1$ is prepared by reducing the corresponding nitrophenyl derivative and optionally acylating or alkylating the thus-obtained product. For the reduction of the nitro group a selective reduction method is to be chosen, which does not saturate either the —C=N— bonds of the 7-membered ring or the vinyl group. So far no method has been described in the literature for the reduction of such compounds. It has been found that hydrazine hydrate applied in the presence of a catalyst is suitable for the selective reduction of compounds of such type. So far hydrazine hydrate in the presence of a catalyst has been used only for the conversion of nitro compounds containing no other reducible group into amino groups [Chem. Rev. 65, 52, (1965); J. Am. Chem. Soc. 75, 4334 (1953); Chem. Lett. 1975, 259].

The reduction is preferably carried out in an organic solvent. Preferably the following solvents or the mixtures thereof can be applied: lower alcohols, dioxane, tetrahydrofurane, benzene, chloroform, dichloromethane, dimethylformamide, dimethyl sulfoxide and pyridine. It is preferable to carry out the reaction with 90–100% hydrazine hydrate applied in excess. As catalyst preferably palladium on bone coal, platinum or Raney nickel is applied. The reaction is carried out at a temperature between 0° C. and the boiling point of the solvent, preferably at a temperature between +10° C. and +100° C.

According to a preferred embodiment of variant b) of the process according to the invention the 1-nitro-styryl-5H-2,3-benzodiazepine derivative of general formula (I) is suspended in methanol and reacted with 2 to 4 equivalents, preferably 3 equivalents of 98–100% hydrazine hydrate in the presence of Raney nickel catalyst at room temperature for 1–2 hour(s). The crude product is separated from the reaction mixture by a method known per se. When the thus-obtained product is hardly soluble in methanol, that is a partial separation occurs, it is preferable to wash the catalyst several times with a solvent, wherein the product can be dissolved readily (such as chloroform). The crude product can be purified by recrystallization or trituration in a solvent. As solvent an alcohol, water or the mixture thereof can be used.

According to a further preferred embodiment of variant b) of the process according to the invention the 1-nitrostyryl-5H-2,3-benzodiazepine derivative of general formula (I) is reacted for 1–2 hours with 3 equivalents of 100% hydrazine hydrate in an alcohol at room temperature, a catalyst and further 2 equivalents of 100% hydrazine hydrate are added to the reaction mixture and it is stirred further for a few hours at room temperature. The mixture is then worked up as specified above.

The aminostyrylbenzodiazepine derivatives of general formula (I) prepared as described above are optionally alkylated or acylated.

The optional alkylation can be performed by methods known per se, preferably with an alkyl halide in an indifferent solvent, in the presence of an acid binding agent, at a temperature between room temperature and the boiling point of the solvent. As solvent preferably aliphatic alcohols, ketones, nitrites, tetrahydrofurane, dioxane, dimethylformamide or dimethyl sulfoxide can be used. As acid binding agent preferably an alkali carbonate, alkali hydrocarbonate or one or two equivalent(s) of a lower tert.amine may be used.

The aminostyrylbenzodiazepines obtained as specified above are optionally acylated. The acylation is carried out by using one or two equivalent(s) of an acid halide or an acid anhydride. The reaction is preferably carried out in the presence of an acid binding agent, preferably in a lower aliphatic tert.amine or in pyridine. It is preferable to carry out the reaction in a solvent (e.g. in an aliphatic ketone, nitrile, tetrahydrofuran, dioxane, pyridine), but the reaction can also be performed without using any solvent, in the excess of the applied reagent.

According to variant c) of the process according to the invention a 5H-2,3-benzodiazepine of general formula (I), wherein A and B together form a group of the formula =C=N—, $R^2$ stands for hydrogen, $R^1$ represents phenyl carrying a fluoro atom, a trifluoromethyl or a cyano group and $R^3$ and $R^4$ together form 7,8- or 8,9-methylenedioxy, is reduced with a complex metal hydride and/or a borane complex. The following reducing agents may be applied: sodium borohydride, lithium aluminium hydride, borane and borane complexes. The reduction is preferably carried out in a solvent. For this purpose water, lower alcohols, lower carboxylic acids, solvents of ether type, aromatic hydrocarbons, chlorinated aliphatic hydrocarbons, pyridine or the mixtures thereof may be used. The solvents or solvent mixtures applicable in a given case depend on the applied reducing agent.

The reduction is carried out at a temperature between 0° C. and 100° C. using preferably 1.1 to 25 molar equivalent(s) of reducing agent.

According to a further embodiment of variant c) of the process according to the invention the starting base of general formula (I) is dissolved or suspended in methanol, an excess of concentrated hydrochloric or acetic acid is added to it, and sodium borohydride is introduced to the thus-obtained hydrochloride or acetate. After working up the reaction mixture the desired 3,4-dihydro compound is obtained by crystallization.

According to a preferred embodiment of variant c) of the process according to the invention 1.5 to 2.0 equivalents of borotrifluoride etherate are added to a solution or suspension of the 5H-2,3-benzodiazepine derivative of general formula (I) in dry dichloromethane, and to the solution of the thus-obtained complex 1.1 equivalent of borane-trimethylamine complex is added. The organic phase is then treated with sodium carbonate, washed with water, dried, evaporated, the desired product is crystallized, filtered and optionally recrystallized from an appropriate solvent, e.g. from a lower alcohol, or suspended in an appropriate solvent.

According to a still further preferred embodiment of process variant c) the compound of general formula (I) is dissolved or suspended in dry tetrahydrofurane, cooled to a temperature between 0° C. and 5° C., 1 molar equivalent of lithium aluminium hydride is added to it and the reaction mixture is stirred at room temperature for 2 hours. The complex is then decomposed and the organic phase is evaporated. The evaporation residue is subjected to column chromatography or crystallization in order to obtain the desired 2,3-benzodiazepines.

Those starting substances of general formula (II), wherein $R^1$ stands for phenyl carrying a fluoro atom a trifluoromethyl or a cyano group, $R^2$ represents hydrogen and $R^3$ and $R^4$ together form a 7,8- or 8,9-methylenedioxy group, have not so far been described in the literature. Both the new and the known compounds can be prepared in a manner analogous to the known synthesis methods provided e.g. in Khim. Geterotsikl. Soedin. 1970, 1308 [C.A. 74, 7629 w (1971)]; 1973, 568, 1458 [C.A. 79, 18629 c (1973), 80, 70649 u (1974).

The new compounds according to the invention possess valuable central nervous activities, particularly anxiolytic, antipsychotic and antiaggressive effects. At the same time they are devoid of any cataleptic side-effect. The majority of the compounds bind to the binding site specific for homoftalazines (2,3-benzodiazepines) [FEBS Letters 308 (2), 215–217 (1992)] with high affinity, which suggests that—assuming a similar absorption and metabolism to those of 2,3-benzodiazepines—they will exert a considerable in vivo activity on the central nervous system.

Surprisingly, the compounds of general formula (I), wherein $R^1$ stands for phenyl carrying a fluoro atom, a trifluoromethyl or a cyano group, $R^2$ represents hydrogen and $R^3$ and $R^4$ together form a 7,8- or 8,9-methylenedioxy group, possess outstanding anxiolytic activity, and at the same time they are practically devoid of any sedative effect. This characteristic is highly advantageous in the therapy of anxiety disorders. These molecules do not bind to the homophtalazine binding site.

The activity of the new compounds is proved by the following experiments.

As reference compounds chlorodiazepoxide (7-chloro-2-methylamino-5-phenyl-3H-1,4-benzodiazepine-4-oxide), diazepam (7-chloro-2,3-dihydro-1-methyl-5-phenyl-1H-1,4-benzodiazepin-2-one) and chlorpromazine [CPZ, 2-chloro-10-(3-dimethylaminopropyl)-phenthiazine] were used. Girisopam [1-(3-chlorophenyl)-4-methyl-7,8-dimethoxy-5H-2,3-benzodiazepine] and nerisopam [1-(4-aminophenyl)-4-methyl-7,8-dimethoxy-5H-2,3-benzodiazepine] were also applied as reference substances, since these compounds also bind to the homophtalazine binding site and have central nervous system activities.

The binding affinity of the new compounds to the homophtalizine binding site was measured by displacing 5 nM of $^3$H-girisopam [1-(3-chlorophenyl)-4-methyl-7,8-dimethoxy-5H-2,3-benzodiazepine] in rat brain striatal membrane preparation. $K_i$ values were calculated according to the following equation:

$$K_i = IC_{50} : \left(1 + \frac{[L]}{K_D}\right)$$

wherein $K_D$ is the dissociation constant of the labelled ligand-receptor complex, [L] is the concentration of the labelled ligand and $IC_{50}$ is the half maximal inhibitory concentration of the test compound. The results are shown in the following Table I.

TABLE I

| Compound (No. of Example) | $K_i$ (nmol/l) |
|---|---|
| 3. | 11 |
| 4. | 11 |
| 5 | 18 |
| 6. | 11 |
| 9. | 18 |
| 10. | 9 |
| 12. | 17 |
| 14. | 16 |
| 15. | 13 |
| 16. | 11 |
| 41. | 16 |
| 42. | 11 |
| 45. | 15 |
| 48. | 19 |
| 49. | 10 |
| 51. | 19 |
| 55. | 11 |
| 57. | 18 |
| 58. | 19 |
| 59. | 16 |
| 18. | 18 |
| 21. | 8 |
| 28. | 12 |
| 33. | 12 |
| 36. | 10 |
| 39. | 14 |

TABLE I-continued

| Compound (No. of Example) | $K_i$ (nmol/l) |
|---|---|
| 65. | 17 |
| 67. | 5 |
| 73. | 11 |
| 74. | 14 |
| 77. | 10 |
| 78. | 11 |
| 84. | 5 |
| 85. | 14 |
| 70. | 13 |
| 71. | 5 |
| girisopam | 40 |
| nerisopam | 16 |

The behavioural effects of the compounds were measured according to the method of Irwin [Phychopharmacology, 13, 222 (1968)].The results and the acute toxicity data (dead/treated animals, shown in brackets) can be seen in Table II.

TABLE II

| Compound | Behaviour (acute toxicity); dose (mg/kg) | | | | | |
|---|---|---|---|---|---|---|
| (No. of Example) | 1000 p.o. | 300 i.p. | 300 p.o. | 100 i.p. | 100 p.o. | 30 i.p. |
| 3 | ++(5/6) | ++(5/6) | +(0/6)[a] | +(0/6) | + | + |
| 4 | ++(1/5) | ++(1/5) | ++ | ++ | ++ | + |
| 5 | ++(0/5) | ++(0/5) | ++ | + | + | +− |
| 6 | +(0/6) | +(0/6) | +[a] | + | | 0 |
| 10 | +(0/6) | +(0/6) | +[a] | +− | | 0 |
| 37 | ++(4/5) | ++(0/5) | ++(0/5) | +− | +− | 0 |
| 38 | ++(1/5) | ++(0/5) | +−(0/5) | +− | 0 | 0 |
| 39 | ++(3/5) | ++(3/5) | ++(0/5) | ++(0/5) | + | +− |
| 40 | ++(4/5) | ++(0/5) | +(0/5) | +− | 0 | 0 |
| 42 | ++(0/5) | ++(0/5) | + | +− | +− | 0 |
| 46 | +−(0/5) | ++(0/5) | 0 | +− | 0 | +− |
| 48 | +−(0/5) | +(0/5) | +− | +− | 0 | 0 |
| 49 | ++(3/5) | ++(0/5) | ++(0/5) | ++ | + | +− |
| 51 | ++(0/6) | +(0/6) | +[a] | 0 | | 0 |
| 54 | +(2/5) | +(2/5) | +−(0/5) | 0(0/5) | 0 | 0 |
| 58 | ++(0/5) | +(0/5) | + | +− | 0 | 0 |
| 64 | +−(0/5) | +(0/5) | +− | +− | 0 | +− |
| 65 | ++(5/5) | ++(0/5) | +(0/5) | +− | +− | 0 |
| 66 | +−(0/5) | +−(0/5) | +− | +− | 0 | 0 |
| 67 | +(0/6) | +−(0/6) | +−[a] | +− | | 0 |
| 77 | ++(0/5) | ++(0/5) | + | +− | 0 | 0 |
| 84 | ++(1/5) | ++(0/5) | ++(0/5) | + | + | +− |
| 85 | +(0/5) | +−(0/5) | + | +− | +− | 0 |
| 70 | +(0/6) | ++(2/6) | +[a] | +(0/6) | | + |
| girisopam | | +−(0/6) | | +− | | 0 |
| nerisopam | | ++(5/6) | | ++(0/6) | | + |

Symbols: ++ strong, + moderate, + slight decrease in SMA, 0: no effect, a: effect of 500 mg/kg p.o. dose From the above Table II it can be seen that the compounds according to the invention considerably decrease the spontaneous motor activity (SMA) in mice after intraperitoneal or oral administration.

The potential antipsychotic activity of the new compounds was tested according to the method of Puech et al. (Psychopharmacology, 75, 84, 1981) by measuring their inhibiting effect on the "climbing" reaction induced by acomorphine. Since the inhibition of the spontaneous motor activity is an important characteristic of the antipsychotic drugs, the $ED_{50}$ values of a number of compounds were determined according to the method of Borsy et al. (Arch. Int. Pharmacodyn., 124, 1, 196). The results obtained are presented in Table III.

TABLE III

| Compound (No. of Example) | SMA ED$_{50}$ mg/kg po. | Apomorfin Climbing ED$_{50}$ mg/kg po. |
|---|---|---|
| 3 | 8.2 | 6.7 |
| 4 | 4.1 | 9.1 |
| 6 | 9.3 | 15 |
| 73 |  | 1.8 |
| 84 |  | 11 |
| girisopam | 10 | 12 |
| nerisopam | 2.5 | 0.9 |
| CDO | 56 | inactive |
| CPZ | 2.0 | 1.1 |

From the results of the above tests it can be established that considering the antipsychotic effect the most active derivatives are nearly as effective as chlorpromazine.

The cataleptic effect of the compounds was measured both in mice (Schlichtegroll: Arzneim. Forsch., 8, 489, 1958) and in rats (Morpurgo: Arch. Int. Pharmacodyn., 137, 87, 1962). The results are shown in Table IV.

TABLE IV

| Compound (No. of Example) | catalepsy in mice MED mg/kg po. | Catalepsy in rats MED mg/kg po. |
|---|---|---|
| 3 | 100 | >100 |
| 4 | >100 | >100 |
| 6 | >100 | >100 |
| 10 | >100 | >100 |
| 21 | >100 | >100 |
| 51 | 100 | >100 |
| 57 | >100 | >100 |
| 67 | >100 | >100 |
| 70 | >100 | >100 |
| nerisopam | 40 | 60 |
| CPZ | 10 | 20 |

On the basis of the above test results it can be established that the compounds according to the invention do not possess cataleptic activity, which would limit their therapeutic application. This fact represents a significant advantage over chlorpromazine and nerisopam posessing a cataleptogenic side-effect.

Furthermore, the new compounds according to the invention on possess significant anxiolytic and antiaggressive effects, too. The anxiolytic activity was studied in rats according to the "lick-conflict" test elaborated by Vogel (Psychopharmacology, 21, 1, 1971) and the elevated plus-maze test described by Pellow (Pellow, J.: Neurosci. Meth. 14, 149, 1985). The antiaggressive effect was investigated in mice using the "fighting behaviour" method of Tedeschi (J. Pharm. Exp. Ther., 125, 28, 1959). The minimal effective dose (MED) values and the ED$_{50}$ values obtained are shown in Table V.

TABLE V

| Compound (No. of Example) | MED (mg/kg) | | | ED$_{50}$ (mg/kg) |
|---|---|---|---|---|
|  | Lick conflict p.o. | Lick conflict i.p. | Elevated + Maze i.p. | Fighting behaviour p.o. |
| 3 | 0.1 |  |  |  |
| 4 | 0.3 | 1.25 | 5.0 | 7.4 |

TABLE V-continued

| Compound (No. of Example) | MED (mg/kg) | | | ED$_{50}$ (mg/kg) |
|---|---|---|---|---|
|  | Lick conflict p.o. | Lick conflict i.p. | Elevated + Maze i.p. | Fighting behaviour p.o. |
| 5 |  | 5.0 | 1.25 | 15 |
| 6 | 1 |  |  |  |
| 10 | 3 |  |  |  |
| 57 | 1 |  |  |  |
| 73 |  | 2.5 | 2.5 | 6.4 |
| 70 | 0.3 |  |  |  |
| CDO | 5 | 3.75 | 2.5 | 9.2 |
| girisopam | 10 |  | 12.5 | 7.7 |
| nerisopam | 0.3 |  | 0.3 | 4.0 |

According to the results of the above experiments the anxiolytic activity of certain test compounds surpasses that of girisopam and chlordiazepoxide by one order of magnitude, while the antiaggressive effect of the new compounds is of similar potency to that of the reference substances.

As it has been mentioned, certain compounds of general formula (I) have outstanding anxiolytic activities and—in contrast to the known 1,4- and 2,3-benzodiazepines—they are practically devoid of any sedative effect. This characteristic is advantageous from the point of view of the therapeutic application. Besides, said compounds exert a weak anticonvulsive activity.

The anxiolytic activity of the above-mentioned group of compounds was investigated in the elevated plus maze test. Male rats belonging to the Sprague Dawley strain and weighing 220 to 260 g were used as test animals. The test was carried out with the aid of a wooden plus-shaped maze elevated to a height of 50 cm and containing two enclosed and two open arms (50 cm long and 15 cm wide). After 60 minutes pretreatment the animals were placed into the maze and observed for 5 minutes. The drug effect was expressed as percent increase of he time spent on the open arms and number of open arm entries. The minimum effective dose (MED) which caused a significant increase of the time spent on the open arms was calculated for every substance [Pelow, S., Chopin, P., File, S. E., Briley, M.: J. Neurosci. Methods 14, 149–167 (1985)]. The data are shown in Table VI.

TABLE VI

| Minimum effective dose | |
|---|---|
| Compound | dose (mg/kg po.) |
| 86 | 0.003 |
| 87 | 0.1 |
| 89 | 0.3 |
| 92 | 1 |
| 90 | 0.3 |
| Diazepam | 1 |

From the above table it can be seen that some compounds according to the invention possess an anxiolytic activity surpassing that of diazepam. The activity of the most effective molecule is highly superior to the reference substance.

The effect of the compounds on the spontaneous motor activity was tested according to the method of Borsy et al. Groups consisting of mice were treated orally with different doses of the compounds to be tested. Then the animals were placed into a 10-channel Dews system equipment, wherein the number of interruptions of infrared beam within 30 minutes was counted. From these data 50% inhibiting doses ($IC_{50}$) were determined with the aid of linear regression [Borsy, J., Csányi, E., Lázár, I.: Arch. . 124, 1 (1960)]. The data are shown in

TABLE VII

| Compound | $IC_{50}$ (mg/kg po.) |
| --- | --- |
| 86 | >100 |
| 87 | >100 |
| 88 | >100 |
| 91 | >100 |
| Diazepam | 23 |

From the data of the above Table it can be seen that when administered in oral doses of 100 mg/kg the test compounds according to the invention practically do not have influence on the spontaneous motor activity of mice (differences within ±12% were observed), contrary to the reference substance having an oral $ID_{50}$ value of 23 mg/kg. Consequently, considering the sedative activity certain compounds according to the invention are much more favourable than diazepam.

The inhibiting effect against convulsions caused by pentetrazole was defined by the modified method of Benziger and Hane. Groups of male and female mice belonging to the NMRI strain and weighing 20 to 25 g were used. The tonic extensor convulsions of the hind limbs caused by intraperitoneally administered 125 mg/kg of pentetrazole were registered on the animals of groups consisting of 6–12 animals. The test compounds and the carrier were administered 1 hour before administering the pentetrazole [Benziger, R., Hane, D.: Arch. Int. Pharmacodyn. 167, 245 (1987)]. The results are given in the following Table VIII.

TABLE VIII

| Compound | Effect 100 mg/kg, p.o. |
| --- | --- |
| 90 | −57% |
| 88 | −44% |
| 91 | −44% |
| Carbamazepine | $IC_{50}$ = 7.1 mg/kg, po. |

According to the test results the compounds according to the invention possess a mild anticonvulsive activity.

According to a further aspect of the present invention there are provided pharmaceutical compositions comprising as active ingredient a compound of general formula (I) or a pharmaceutically acceptable acid addition salt thereof in admixture with suitable inert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatin capsule, solution, emulsion or suspension), parenteral (e.g. injection solution) or rectal (e.g. suppository) administration.

As carrier for the preparation of tablets, coated tablets, dragées and solid gelatin capsules e.g. lactose, corn starch, potato starch, talc, magnesium carbonate, magnesium stearate, calcium carbonate, stearic acid or the salts thereof, etc. can be used. As carrier for the soft gelatin capsules e.g. vegetable oils, fats, waxes or polyols of suitable consistency can be used. As carriers for the solutions and syrups e.g. water, polyols (polyethylene glycol), saccharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition, the pharmaceutical formulations may comprise auxiliaries usually applied in pharmaceutical industry, e.g. wetting, sweetening agents, aroma substances, salts causing the change of osmotic pressure, buffers etc. The pharmaceutical formulations may further comprise other active ingredients, too.

The daily dose of the compounds of general formula (I) can vary within wide ranges depending on several factors, e.g. on the activity of the active ingredient, the patient's condition and age, the severity of the disease etc. The preferred oral dose is generally 0.1 to 500 mg/day. It has to be stressed that the above dose is only of informative character and the administered dose must always be determined by the physician therapeutist.

According to a further aspect of the present invention there is provided the use of the compounds of general formula (I) or pharmaceutically acceptable acid addition salts thereof for the preparation of pharmaceutical compositions affecting particularly the central nervous system.

According to a still further aspect of the present invention there is provided a method for the treatment of central nervous system disorders, which comprises administering to a patient an effective amount of a compound of general formula (I) or a pharmaceutically acceptable acid addition salt thereof.

Further details of the present invention are to be found in the following Examples without limiting the scope of protection to the said Examples.

EXAMPLE 1

1-(4-Bromostyryl)-4-methyl-7,8-dimethoxy-5H-2, 3-benzodiazepine

To a suspension of 4.6 g (9.47 mmoles) of powdered 1-(4-bromostyryl)-3-methyl-6,7-dimethoxy-2-benzopyrilium perchlorate [m.p.: 274–275° C. (decomp.)] in 46 ml of 99.5% ethanol 1.4 ml (28.4 mmoles) of 100% hydrazine hydrate is added, and the mixture is stirred until complete dissolution. Then it is allowed to stand at 25° C. for half an hour and then evaporated in vacuo. The residue is solidified in 100 ml of water, filtered, washed three times with 15 ml each of water, the crude product is suspended while hot in 400 ml of water for 30 minutes, filtered, washed three times with 15 ml each of water and dried at 80–100° C. Thus 2.8 g of crude product are obtained. In order to purify the crude product it is boiled ill 15 ml of ethanol, cooled, filtered, washed three times with 1 ml each of ethanol and dried. Thus 2.26 g (60%) of the desired product are obtained. M.p.: 156–158° C.

EXAMPLE 2

1-(4-Nitrostyryl)-4-methyl-5-ethyl-7,8-dimethoxy-5H-2,3-benzodiazepine

To a suspension of 1.58 g (3.3 mmoles) of powdered 1-(4-nitrostyryl)-3-methyl-4-ethyl-6,7-dimethoxy-2-benzopyrilium perchlorate [m.p.: 277–278° C., (decomp.)] in 16 ml of 99.5% ethanol 0.5 ml (10.0 mmoles) of 100% hydrazine hydrate is added, and the mixture is stirred at 25° C. for 1 hour. After stirring for 10 to 15 minutes the desired product begins to separate from the solution in crystalline form. The mixture is stirred further for one hour, the product is filtered, washed successively three times with 1 ml each of ethanol and three times with 5 ml each of water and dried at a temperature between 80° C. and 100° C. Thus 1.10 g of the desired product is obtained. M.p.: 218–220° C. (decomp.).

In order to purify the crude product it is boiled in 5 ml of ethanol, cooled, filtered, washed three times with 1 ml each of ethanol and dried. Thus 1.03 g (80.0%) of the desired product is obtained. M.p.: 220–221° C. (decomp.).

EXAMPLE 3

1-(3,4-Dimethoxystyryl)-4-methyl-7,8-dimethoxy-5H-2,3-benzodiazepine

Method A 4.0 g (8.56 mmoles) of 1-(3,4-dimethoxystyryl)-3-methyl-6,7-dimethoxy-2-benzopyrilium perchlorate are suspended in 80 ml of ethanol, 1.3 ml (25.7 mmoles) of 100% hydrazine hydrate is added to the suspension and the reaction mixture is refluxed for 5 minutes. The solution is then evaporated in vacuo. Further on the procedure of Example 1 is followed. Thus 1.5 g (46.6%) of the desired product is obtained. M.p.: 156–158° C.

Method B

To a mixture of 0.32 ml (6.42 mmoles) of 100% hydrazine hydrate and 5 ml of dimethyl formamide 1.0 g (2.14 mmoles) of 2-benzopyrilium perchlorate prepared as described above are added within 5 minutes under cooling with tap water. The thus-obtained solution is stirred for 0.5 hours, poured into 100 ml of 15% aqueous sodium chloride solution and the separated crude product is extracted with chloroform. The chloroform phase is dried and evaporated in vacuo.

Thus 0.86 g of crude product is obtained. In order to purify the crude product it is recrystallized from 4 ml of ethanol, suspended in 20 ml of hot water, filtered, washed with hot water and dried. Thus 0.59 g (71.9%) of the desired product is obtained in pure form. M.p.: 156–158° C.

Method C 1.0 g (2.14 mmoles) of 2-benzopyrilium perchlorate prepared as described above is boiled in a mixture of 20 ml of chloroform and 0.32 ml (6.42 mmoles) of 100% hydrazine hydrate for 30 minutes. Thus a solution is obtained. The solvent is then evaporated and the residue is triturated with 40 ml of hot water, the crude product is dried and recrystallized from 3 ml of ethanol. Then it is suspended in 25 ml of hot water, filtered, washed three times with 1 ml each of hot water and dried. Thus 0.21 g (25.6%) of pure title compound is obtained. M.p.: 156–158° C.

Method D

A mixture of 2.0 g (4.28 mmoles) of 2-benzopyrilium perchlorate prepared as described above, 4 ml of pyridine and 0.65 ml (12.8 mmoles) of 100% hydrazine hydrate is stirred at room temperature for 1 hour. The reaction mixture is then poured into 100 ml of water, the separated precipitate is filtered, washed three times with 10 ml of hot water, the crude product is dried and recrystallized from 10 ml of ethanol. Thus 1.06 g (64.6%) of the desired compound is obtained. M.p.: 156–158° C.

Method E

A mixture of 2.0 g (4.28 mmoles) of benzopyrilium perchlorate prepared as described above, 4 ml of tetrahydrofuran and 0.64 ml (12.84 mmoles) of 100% hydrazine hydrate is refluxed for 30 minutes. The suspension is then cooled to room temperature, filtered, the filtrate is poured into 100 ml of water, the separated product is extracted with 15 ml of chloroform, and then the purification procedure described in Example 2 is carried out. Thus 0.37 g (22.6%) of the desired compound is obtained. M.p.: 156–158° C.

Method F

A mixture of 2.0 g (4.28 mmoles) of 2-benzopyrilium perchlorate prepared as described above, 20 ml of benzene and 0.64 ml (12.84 mmoles) of 100% hydrazine hydrate is refluxed for 7 hours. Then it is filtered at 25° C., the filtrate is evaporated and the residue is boiled for 30 minutes in 20 ml of water, decanted while hot and the crude product is recrystallized from 5 ml of ethanol. Thus 0.83 g (50.6%) of the desired compound is obtained. M.p.: 156–158° C.

Method G

On starting from a mixture of 2.0 g (4.28 mmoles) of 2-benzopyrilium perchlorate prepared as described above, 4 ml of dimethyl sulfoxide and 0.64 ml (12.84 mmoles) of 100% hydrazine hydrate and proceeding as specified in method B above 1.2 g (73.6%) of the desired compound is obtained. M.p.: 156–158° C.

EXAMPLE 4

1-(4-Dimethylaminostyryl)-4-methyl-7,8-dimethoxy-5H-2,3-benzodiazepine

A mixture of 80.0 ml of dimethylformamide and 5.7 ml (114.0 mmoles) of 100% hydrazine hydrate is cooled with tap water, and 17.07 g (37.9 mmoles) of 1-(4-dimethylaminostyryl)-3-methyl-6,7-dimethoxy-2-benzopyrilium perchlorate (m.p.: 245–246° C., decomp.) are added to it. The thus-obtained solution is then stirred for 40 minutes and dropped to 800 ml of water. The separated crude product is filtered, washed three times with 60 ml each of water and dried at a temperature between 80° C. and 100° C. Thus 12.9 g of the desired product are obtained. In order to purify it the product is boiled with 100 ml of 50% ethanol for 15 minutes, the suspension is cooled to room temperature, filtered, washed three times with 15 ml each of 50% ethanol and dried. Thus 10.5 g (76.3%) of desired compound are obtained. M.p.: 170–172° C.

EXAMPLE 5

1-(2,4-Dimethoxystyryl)-4-methyl-7,8-dimethoxy-5H-2,3-benzodiazepine

A mixture of 21.5 ml of dimethylformamide and 2.3 ml (46.0 mmoles) of 100% hydrazine hydrate is cooled with tap water, and 7.15 g (15.3 mmoles) of 1-(2,4-dimethoxystyryl)-3-methyl-6,7-dimethoxy-2-benzopyrilium perchlorate (m.p.: 270–271° C., decomp.) are added to it within 15 minutes. The thus-obtained yellowish solution is stirred further for 30 minutes and then 43 ml of water are dropped to it under cooling, whereupon the end-product begins to separate. The thus-obtained crystalline mush is kept at 5° C. for 12 hours, filtered, washed three times with 20 ml each of water and dried at a temperature between 80° C. and 100° C. Thus 5.18 g of the desired product are obtained. M.p.: 148–150° C.

After recrystallization from 26 ml of ethanol 5.01 g (86.1%) of the desired compound are obtained. M.p.: 151–153° C.

Further compounds of general formula (I) have also been prepared according to the methods of Examples 1 to 5, which are summarized in the following Table IX.

| Example | R¹ | R² | R³ | R⁴ | Reference example | Yield % | M.p. ° C. (recrystallization) |
|---|---|---|---|---|---|---|---|
| 6. | 3,4,5-trimethoxyphenyl | H | Me | Me | 1. | 65.6% | 185–187 (EtOH) |
| 7. | 2-nitrophenyl | H | Me | Me | 1. | 70.% | 178–180 (EtOH) |
| 8. | 3,4,5-trimethoxyphenyl | Et | OCH₃ | OCH₃ | 1. | 60.0% | 135–136 (i-PrOH) |
| 9. | 4-methoxyphenyl | H | OCH₃ | OCH₃ | 1. | 65.0% | 140–142 (EtOH) |
| 10. | 2-fluorophenyl | H | Me | Me | 1. | 56.0% | 146–148 (EtOH) |
| 11. | 4-nitrophenyl | H | Et | Et | 1. | 83.6% | 172–174 (EtOH) |
| 12. | 4-nitrophenyl | H | Me | Me | 1. | 65.3% | 166–168 (EtOH) |
| 13. | 2,4-dichlorophenyl | H | Me | Me | 1. | 64.0% | 180–182 (EtOH) |
| 14. | 3-methyl-4-methoxyphenyl | H | Me | Me | 1. | 68.1% | 160–161 (EtOH) |
| 15. | 4-isopropoxyphenyl | H | Me | Me | 1. | 40.2% | 125–128 (EtOH) |
| 16. | 3-isopropoxyphenyl | H | Me | Me | 1. | 42.2% | 140–142 (EtOH) |
| 17. | 4-isopropoxyphenyl | H | —CH₂— | | 1. | 55.1% | 200–202 (EtOH) |
| 18. | 2-isopropoxyphenyl | H | Me | Me | 1. | 45.2% | 125–127 (EtOH) |
| 19. | 4-isopropoxyphenyl | Et | Me | Me | 1. | 50.6% | 120–122 (50% EtOH) |
| 20. | 4-ethoxyphenyl | H | Me | Me | 1. | 61.9% | 158–160 (decomp.) (DMF) |
| 21. | 2-methoxy-3,4-methylenedioxyphenyl | H | Me | Me | 2. | 46.6 | 160–164 (decomp.) (EtOH) |
| 22. | 2,3-methylenedioxy-4-methoxyphenyl | H | Me | Me | 2. | 50.0% | 204–205 (EtOH) |
| 23. | 3,4-dihydroxyphenyl | H | Me | Me | 2. | 72.2% | 231–232 (EtOH) |
| 24. | 1-naphtyl | H | Me | Me | 2. | 60.2% | 220–224 (EtOH) |
| 25. | 3-nitrophenyl | H | Me | Me | 2. | 86.6% | 180–182 (decomp.) (DMF) |
| 26. | 2-nitro-4,5-dimethoxyphenyl | H | Me | Me | 2. | 70.0% | 194–195 (decomp.) (EtOH) |
| 27. | 3,4-dichlorophenyl | H | Me | Me | 2. | 82.0% | 168–169 (DMF H₂O 1:1) |
| 28. | 4-fluorophenyl | H | Me | Me | 2. | 7.0% | 155–157 (EtOH) |
| 29. | 2-nitro-5-chlorphenyl | H | Me | Me | 2. | 74.1% | 209–210 (decomp.) (EtOH) |
| 30. | 2,6-dichlorophenyl | H | Me | Me | 2. | 83.1% | 158–160 (EtOH) |
| 31. | 4-nitrophenyl | H | —CH₂— | | 4. | 72.0% | 227–228 (decomp.) (DMF) |
| 32. | 3-nitrophenyl | H | —CH₂— | | 4. | 71.0% | 216–218 (decomp.) (DMF) |
| 33. | phenyl | H | Me | Me | 4. | 75.4% | 143–145 (EtOH) |
| 34. | 3,4,5-trimethoxyphenyl | H | —CH₂— | | 4. | 86.4% | 190–192 (EtOH) |
| 35. | 3-nitro-4-chlorophenyl | H | Me | Me | 4. | 72.0% | 197–198 (EtOH) |
| 36. | 2-bromophenyl | H | Me | Me | 4. | 80.0% | 176–178 (EtOH) |
| 37. | 4-dimethylaminophenyl | Et | Me | Me | 4. | 93.4% | 134–136 (EtOH) |
| 38. | 3,4,5-trimethoxyphenyl | H | Et | Et | 4. | 70.1% | 148–150 (50% EtOH) |
| 39. | 4-dimethylaminophenyl | H | Et | Et | 4. | 82.2% | 158–160 (50% EtOH) |
| 40. | 3-isopropyl-4-methoxyphenyl | H | Me | Me | 4. | 87.0% | 156–158 (EtOH) |
| 41. | 3-propyl-4-methoxyphenyl | H | Me | Me | 4. | 68.9% | 115–117 (50% EtOH) |
| 42. | 2-methylphenyl | H | Me | Me | 4. | 82.5% | 154–156 (decomp.) (EtOH) |
| 43. | 3-isopropyl-4-methoxyphenyl | H | —CH₂— | | 4. | 76.7% | 155–157 (EtOH) |
| 44. | 3-isopropyl-4-methoxyphenyl | H | Et | Et | 4. | 60.0% | 114–116 (50% EtOH) |
| 45. | 4-trifluoromethylphenyl | H | Me | Me | 4. | 65.0% | 178–179 (EtOH) |
| 46. | 3-chlorophenyl | H | —CH₂— | | 4. | 57.3% | 135–137 (EtOH) |
| 47. | phenyl | Et | Me | Me | 4. | 78.3% | 152–154 (EtOH) |
| 48. | 3-chlorophenyl | Et | Me | Me | 4. | 70.6% | 143–145 (EtOH) |
| 49. | 4-diethylaminophenyl | H | Me | Me | 4. | 65.0% | 168–170 (EtOH) |
| 50. | 4-nitrophenyl | H | Me | Me | 5. | 73.0% | 224–226 (decomp.) (EtOH) |
| 51. | 3-chlorophenyl | H | Me | Me | 5. | 79.2% | 178–180 (DMF H₂O 1:1) |
| 52. | 3,4-dimethoxyphenyl | H | —CH₂ | | 5. | 89.5% | 206–208 (EtOH) |
| 53. | 2,3-dimethoxyphenyl | H | Me | Me | 5. | 76.7% | 137–138 (EtOH) |
| 54. | 2-chlorophenyl | H | Me | Me | 5. | 63.5% | 158–160 (EtOH) |
| 55. | 3-chloro-4-methoxyphenyl | H | Me | Me | 5. | 92.7% | 205–207 (EtOH) |
| 56. | 4-dimethylaminophenyl | H | —CH₂ | | 5. | 87.1% | 219–222 (decomp.) (EtOH) |
| 57. | 4-cyanophenyl | H | Me | Me | 5. | 75.0% | 185–186 (EtOH) |
| 58. | 2,4,6-trimethoxyphenyl | H | Me | Me | 5. | 84.7% | 191–193 (EtOH) |
| 59. | 2,4,5-trimethoxyphenyl | H | Me | Me | 5. | 78.4% | 148–150 (EtOH) |
| 60. | 3,4-methylenedioxyphenyl | H | —CH₂— | | 5. | 82.6% | 223–225 (decomp.) (EtOH) |
| 61. | 2,3-dimethoxyphenyhl | H | —CH₂— | | 5. | 82.0% | 149–150 (EtOH) |
| 62. | 2,4-dimethoxyphenyl | H | —CH₂— | | 5. | 92.6% | 210–211 (decomp.) (EtOH) |
| 63. | phenyl | H | —CH₂— | | 5. | 77.8% | 153–154 (EtOH) |
| 64. | 2,3-dimethoxyphenyl | Et | Me | Me | 5. | 68.3% | 158–160 (EtOH) |
| 65. | 3,4-dimethoxyphenyl | H | Et | Et | 5. | 73.1% | 126–127 (EtOH) |
| 66. | 3,4-dichlorphenyl | H | —CH₂— | | 5. | 80.0% | 175–176 (EtOH) |
| 67. | 3,4-methylenedioxyphenyhl | H | Me | Me | 5. | 86.5% | 158–160 (EtOH) |
| 68. | 2-hydroxy-1-naphtyl | H | Me | Me | 5. | 63.1% | 236–238 (EtOH) |
| 69. | 4-ethoxycarbonylphenyl | H | Me | Me | 2. | 67.6% | 196–200 (EtOH) |
| 70. | 2-thienyl | H | Me | Me | 2. | 58.9% | 127–132 (EtOH) |
| 71. | 3-indolyl | H | Me | Me | 2. | 67.6% | 214–219 (EtOH) |
| 72. | 2-furyl | H | Me | Me | 2. | 30.0% | 149–150 (EtOH) |

EXAMPLE 73

1-(4-Aminostyryl)-4-methyl-7,8-dimethoxy-5H-2,3-benzodiazepine

Method A 4.0 g (10.9 mmoles) of 1-(4-nitrostyryl)-4-methyl-7,8-dimethoxy-5H-2,3-benzodiazepine (the compound of Example 50) are suspended in 100 ml of methanol, 0.4 g of dry (or about 0.8 g of wet) Raney nickel catalyst and 1.63 ml (32.7 mmoles) of 100% hydrazine hydrate are added to the suspension and the reaction mixture is stirred for 1 hour. Thus a solution is obtained, and the inner temperature rises to 40 to 45° C. The catalyst is filtered off and washed three times with 15 ml each of methanol, the filtrates are combined and evaporated in vacuo, the crude product is added to 50 ml of water, filtered, washed three times with 15 ml each of water and dried. Thus 3.5 g of the desired compound are obtained. In order to purify the crude product it is recrystallized from 35 ml of 50% ethanol. Thus 3.17 g (86.4%) of the desired product are obtained. M.p.: 196–198° C. (decomp.).

The hydrochloride salt is prepared as follows: 0.34 g of base is suspended in 4 ml of hot water, 0.10 ml of concentrated hydrogen chloride is added to it and the solution is cooled quickly. Yield: 0.30 g (80.0%). M.p.: 227–228° C. (decomp.).

Method B 4.25 g (10 mmoles) of 1-(4-nitrostyryl)-3-methyl-6,7-dimethoxybenzopyrilium perchlorate (m.p.: 273–274° C., decomp.) are suspended in 150 ml of methanol, 1.5 ml (30 mmoles) of 100% hydrazine hydrate is added to the suspension and it is stirred at room temperature for 2 hours. From the thus-obtained solution yellow crystals (the compound of Example 50) begin to separate in about 5 minutes. Then about 0.4 g of dry (or about 0.8 g of wet) Raney nickel catalyst and 1.0 ml (20 mmoles) of 100% hydrazine hydrate are added to the reaction mixture and it is stirred for 1–2 hour(s) (until the gas evolution has ceased). The catalyst is then filtered off, washed three times with 10 ml each of methanol, the filtrate is evaporated in vacua using a water bath having a temperature not exceeding 25° C. The residue is added to 50 ml of water, filtered, the crude product is washed three times with 15 ml each of water and dried at a temperature between 60° C. and 70° C. Thus 3.05 g of the desired product are obtained. M.p.: 148–155° C.

In order to purify the crude product it is recrystallized from 10 ml of 50% ethanol and suspended first in 200 ml then in 150 ml of hot water, filtered at once, washed three times with 10 ml each of water and dried at a temperature between 80° C. and 100° C. Thus 1.37 g (41%) of the title product is obtained. M.p.: 196–198° C. (decomp.).

The following compounds of general formula (I) summarized in the following Table X were prepared according to method A of Example 73.

TABLE X

| Example | $R^1$ | $R^2$ | $R^3$ | $R^4$ | Solvent to wash the example | Yield % | M.p. ° C. (recrystallization) |
|---|---|---|---|---|---|---|---|
| 74. | 3-aminophenyl | H | Me | Me | $CHCl_3$ | 73.5 | 155–157 (50% EtOH) |
| 75. | 4-aminophenyl | H | —$CH_2$— | | MeOH | 71.0 | 184–186 (EtOH) |
| 76. | 3-aminophenyl | H | —$CH_2$— | | MeOH | 70.0 | 195–196 (EtOH) 2 HCl Salt: 225 (decomp.) |
| 77. | 3-amino-4-chlorophenyl | H | Me | Me | MeOH | 78.0 | 180–182 (decomp) (EtOH) |
| 78. | 4-aminophenyhl | H | Et | Et | MeOH | 69.5 | 128–130 (50% EtOH) |
| 79. | 2-aminophenyl | H | Me | Me | MeOH | 76.5 | 217–219 (decomp.) (EtOH) |
| 80. | 2-amino-5-chlorophenyl | H | Me | Me | $CHCl_3$ | 65.0 | 213–215 (decomp.) (EtOH) |
| 81. | 4-aminophenyl | Et | Me | Me | MeOH | 90.0 78.0 | monohydrate: 102–104 (EtOH/$H_2O$) 2 HBr salt: 221–223 (decomp.) (i-PrOH) |
| 82. | 2-amino-4,5-dimethoxyphenyl | H | Me | Me | MeOH | 43.6 | 200–201 (decomp.) (EtOH) |

EXAMPLE 83

1-(4-Acetylaminostyryl)-4-methyl-7,8-methylenedioxy-5H-2,3-benzodiazepine 4.0 g (12.5 mmoles) of 1-(4-aminostyryl)-4-methyl-7,8-methylenedioxy-5H-2,3-benzodiazepine (the compound of Example 68) are suspended in 20 ml of acetic anhydride. The suspension is stirred at room temperature for 1 hour. In the meantime the starting substance gets dissolved, the desired product begins to separate and the reaction mixture becomes thick. The separated product is filtered, washed three times with 25 ml each of diethyl ether and dried at a temperature between 80° C. and 100° C. Thus 4.0 g of the desired product are obtained. In order to purify the crude product it is boiled in 15 ml of 50% ethanol for 15 minutes, cooled, filtered, washed three times with 5 ml each of 50% ethanol and dried at a temperature between 80° C. and 100° C. Thus 3.87 g (85.6%) of the desired product are obtained. M.p.: 218–220° C. (decomp.).

The new compounds of the following Examples 84 and 85 were prepared according to the method specified in Example 83.

EXAMPLE 84

1-(4-Acetylaminostyryl)-4-methyl-7,8-dimethoxy-5H-2,3-benzodiazepine

Yield: 88.9%. M.p.: 208–210° C. (decomp.). (50% ETOH)

EXAMPLE 85

1-(3-Acetylamino-4-chlorostyryl)-4-methyl-7,.8-dimethoxy-5H-2,3-benzodiazepine Yield: 87.7%. M.p.: 202–204° C. (decomp.) (50% EtOH)

EXAMPLE 86

1-(4-Fluorostyryl)-4-methyl-7,8-methylenedioxy-5H-2,3-benzodiazepine

To a suspension of 15.1 g (37 mmoles) of powdered 1-(4-fluorostyryl)-3-methyl-6,7-methylenedioxy-2- benzopyrilium perchlorate in 150 ml of methanol 4.1 ml (82 mmoles) of hydrazine hydrate are added, and the mixture is stirred until complete dissolution. Then it is allowed to stand for 1 hour at 25° C., evaporated in vacuo, the residue is stirred in the mixture of 50 ml of water and 50 ml of ethyl acetate. The ethyl acetate phase is separated, dried over magnesium sulfate and the solvent is evaporated in vacuo. The residue is dissolved in 50 ml of ethanol and the end-product is separated from the ethanol solution by adding some water to it. Thus 8.9 g of crude product are obtained, which is recrystallized from ethanol. Thus 8.1 g (68%) of substance pure on TLC are obtained. M.p.: 141–144° C.

EXAMPLE 87

1-(4-Trifluoromethylstyryl)-4-methyl-7,8-methylenedioxy-5H-2,3-benzodiazepine

To a suspension of 9.17 g (20 mmoles) of powdered 1-[(4-trifluoromethyl)-styryl]-3-methyl-6,7-(methylenedioxy)-2-benzopyrilium perchlorate in 100 ml of methanol 2.5 ml (50 mmoles) of hydrazine hydrate are added, and the reaction is carried out as specified in Example 86. Thus 6.7 g of crude product are obtained, which is purified by recrystallization from ethanol. Thus 6.1 g (82%) of the desired substance pure on TLC are obtained. M.p.: 188–191° C.

EXAMPLE 88

1-(4-Cyanostyryl)-4-methyl-7,8-methylenedioxy-5H-2,3-benzodiazepine

To a suspension of 9.30 g (23.1 mmoles) of 1-(4-cyanostyryl)-3-methyl-6,7-methylenedioxy-2-benzopyrilium perchlorate prepared according to Example 95 in 100 ml of methanol 3.5 ml (70 mmoles) of hydrazine hydrate are dropped, under stirring. The reaction mixture is stirred at room temperature for 3 hours at room temperature, filtered and some water are added to the filtrate under stirring. The separated crystals are filtered off and recrystallized from ethanol. Thus 2.90 g (38%) of the desired compound are obtained. M.p.: 197.5–202.5° C.

EXAMPLE 89

1-(3-Fluorostyryl)-4-methyl-7,8-methylenedioxy-5H-2,3-benzodiazepine 8.17 g (0.02 mole) of 1-(3-fluorostyryl)-3-methyl-6,7-methylenedioxy-2-benzopyrilium perchlorate prepared according to Example 96 are suspended in 100 ml of methanol and 2.5 ml (0.05 mole) of hydrazine hydrate are dropped to the suspension. Then the reaction mixture is stirred at room temperature for 2 hours, filtered and the filtrate is evaporated. The residue is dissolved in the mixture of 50 ml of water and 50 ml of ethyl acetate, the organic phase is separated, dried over magnesium sulfate and evaporated again. The residue is crystallized from ethanol and recrystallized from acetonitrile. Thus 4.30 g (67%) of the desired product are obtained, which is pure on TLC. M.p.: 161–162° C.

EXAMPLE 90

1-(2-Fluorostyryl)-4-methyl-7,8-methylenedioxy-5H-2,3-benzodiazepine 8.17 g (0.02 mole) of 1-(2-fluorostyryl)-3-methyl-6,7-methylenedioxy-2-benzopyrilium perchlorate prepared according to Example 97 are stirred in 100 ml of acetonitrile, and 2.5 ml (0.05 mole) of hydrazine hydrate are dropped to the mixture. It is stirred further for 2 hours at room temperature, filtered and the filtrate is evaporated. The evaporation residue is dissolved in the mixture of 50 ml of water and 50 ml of ethyl acetate, the organic phase is separated, dried over magnesium sulfate and evaporated again. The residue is crystallized from ethanol and purified by recrystallization from ethanol. Thus 3.79 g (59%) of the desired compound are obtained, which is pure on TLC and melts at 138–141° C.

EXAMPLE 91

1-(4-Fluorostyryl)-4-methyl-8,9-methylenedioxy-5H-2,3-benzodiazepine 2.70 g (6.6 mmoles) of 1-(4-fluorostyryl)-3-methyl-7,8-methylenedioxy-2-benzopyrilium perchlorate prepared according to Example 98 are stirred in 50 ml of acetonitrile, and 0.80 ml (16.0 mmole) of hydrazine hydrate are dropped to the mixture. Then it is stirred further for 2 hours at room temperature, filtered and the filtrate is evaporated. The evaporation residue is dissolved in the mixture of 10 ml of water and 10 ml of ethyl acetate. The organic phase is separated, dried over magnesium sulfate and evaporated again. The product is obtained from the evaporation residue by purification on a Kieselgel 60 column. Thus 1.10 g (52%) of the desired substance pure on TLC is obtained.

EXAMPLE 92

1-(4-Fluorostyryl)-4-methyl-7,8-methylenedioxy-3,4-dihydro-5H-2,3-benzodiazepine To a mixture of 2.0 g (6.2 mmoles) of 1-(4-fluorostyryl)-4-methyl-7,8-methylenedioxy-5H-2,3-benzodiazepine prepared according to Example 86 and 10 ml of glacial acetic acid a solution of 3.0 g (79 mmoles) of sodium borohydride in 10 ml of water is added in small portions, while the temperature of the reaction mixture is kept below 35° C. The mixture is then stirred for further 2 hours and made alkaline by adding some sodium carbonate solution to it. The alkaline solution is extracted three times with 20 ml of ethyl acetate. The ethyl acetate phases are dried, evaporated and the evaporation residue is crystallized from ethanol. The crude product is purified by recrystallization from ethanol. Thus 1.39 g (69%) of substance pure on TLC is obtained. M.p.: 170–174° C.

Preparation of the new starting substances:

EXAMPLE 93

1-(4-Fluorostyryl)-3-methyl-6,7-methylenedioxy-2-benzopyrilium perchlorate

A mixture of 15.10 g (0.05 mole) of 1,3-dimethyl-6,7-methylenedioxy-2-benzopyrilium perchlorate, 80 ml of glacial acetic acid and 6.20 g (0.05 mole) of 4-fluorobenzaldehyde is stirred on an oil bath of 150° C. for 3 hours. The reaction mixture is cooled to 80° C., filtered, the precipitate is washed twice with 10 ml each of acetic acid and twice with 30 ml each of ethyl acetate and dried at room temperature. Thus 9.60 g (47%) of the desired product decomposing at about 203–204° C. are obtained. The substance can be used for the further reactions without any purification.

EXAMPLE 94

1-(4-Trifluoromethylstyryl)-3-methyl-6,7-methylenedioxy-2-benzopyrilium perchlorate A mixture of 15.10 g (0.05 mole) of 1,3-dimethyl-6,7-methylenedioxy-2-benzopyrilium perchlorate, 80 ml of glacial acetic acid and 8.70 g (0.05 mole) of 4-trifluoromethyl benzaldehyde is stirred on an oil bath of 150° C. for 3 hours. Then the reaction mixture is worked up as specified in Example 1. Thus 13.30 g (58%) of the desired product decomposing at 197–201° C. are obtained, which can be used for the further reactions without any purification.

EXAMPLE 95

1-(4-Cyanostyryl)-3-methyl-6,7-methylenedioxy-2-benzopyrilium perchlorate

A mixture of 9.33 g (0.031 mole) of 1,3-dimethyl-6,7-methylenedioxy-2-benzopyrilium perchlorate, 50 ml of glacial acetic acid and 4.0 g (0.032 mole) of 4-cyanobenzaldehyde is stirred on an oil bath of 150° C. for 3 hours. Then it is worked up as specified in Example 86. Thus 9.30 g (75%) of the desired product decomposing at 241–247° C. are obtained.

EXAMPLE 96

1-(3-Fluorostyryl)-3-methyl-6,7-methylenedioxy-2-benzopyrilium perchlorate

A mixture of 15.10 g (0.05 mole) of 1,3-dimethyl-6,7-methylenedioxy-2-benzopyrilium perchlorate, 80 ml of glacial acetic acid and 6.20 g (0.05 mole) of 3-fluorobenzaldehyde is stirred on an oil bath of 150° C. for 3 hours. The mixture is then worked up as specified in Example 86. Thus 11.20 g (55%) of the desired product decomposing at 186–190 ° C. are obtained.

EXAMPLE 97

1-(2-Fluorostyryl)-3-methyl-6,7-methylenedioxy-2-benzopyrilium perchlorate

A mixture of 15.10 g (0.05 mole) of 1,3-dimethyl-6,7-methylenedioxy-2-benzopyrilium perchlorate, 80 ml of glacial acetic acid and 6.20 g (0.05 mole) of 2-fluorobenzaldehyde is stirred on an oil bath of 150° C. for 3 hours. The reaction mixture is then worked up as specified in Example 86. Thus 10.0 g (49%) of the desired product decomposing at 235–238° C. are obtained, which can be used for the further reactions without any purifications.

EXAMPLE 98

1-(4-Fluorostyryl)-3-methyl-7,8-methylenedioxy-2-benzopyrilium perchlorate

A mixture of 5.0 g (16.6 mmole) of 1,3-dimethyl-7,8-methylenedioxy-2-benzopyrilium perchlorate, 30 ml of glacial acetic acid and 2.10 g (16.6 mmoles) of 4-fluorobenzaldehyde is stirred on an oil bath of 150° C. for 1 hour. The reaction mixture is then worked up as specified in Example 86. Thus 2.70 g (40%) of the desired compound decomposing at 205–209° C. are obtained, which can be used for the further reactions without any purification.

What we claim is:

1. 1-[2-(Substituted vinyl)]-5H-2,3-benzodiazepine derivatives comprising the formula (I),

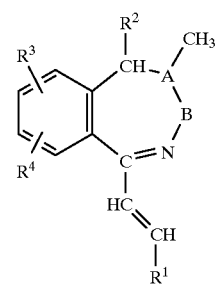

wherein

A and B together form a group of the formula =C=N— or =CH—NH—;

$R^1$ represents phenyl optionally carrying 2 or 3 hydroxy groups or 1 to 3 identical or different substituent(s) selected from the group consisting of halogen, trifluoromethyl, nitro, cyano, amino, $C_{1-3}$ alkylamino, di(-$C_{1-3}$ alkyl)-amino, $C_{1-4}$ alkanoylamino, $C_{1-4}$ alkyl, $C_{1-4}$ alkoxy, carboxy, ($C_{1-4}$-alkoxy)-carbonyl, $C_1$–$C_4$ alkoxycarbonyloxy and methylenedioxy; naphtyl optionally carrying a substituent selected from the group consisting of hydroxy, $C_{1-4}$ alkoxy and $C_{1-4}$ acyloxy; furyl, thienyl or indolyl;

$R^2$ stands for hydrogen or $C_{1-4}$ alkyl;

$R^3$ and $R^4$ each represents $C_{1-4}$ alkoxy attached to positions 7 and 8 of the benzodiazepine ring, or $R^3$ and $R^4$ together form a 7,8- or 8,9-methylenedioxy group, or pharmaceutically acceptable acid addition salts thereof.

2. 1-[2-(Substituted vinyl)]-5H-2,3-benzodiazepine derivatives of formula (I) as defined in claim 1, wherein A and B together form a group of the formula =C=N—;

$R^1$ represents phenyl optionally carrying 2 or 3 hydroxy groups or 1 to 3 identical or different substituent(s) selected from the group consisting of halogen, trifluoromethyl, nitro, cyano, amino, $C_{1-3}$ alkylamino, di-($C_{1-3}$ alkyl)-amino, $C_{1-4}$ alkanoylamino, $C_{1-4}$ alkyl, $C_{1-4}$ alkoxy, carboxy, ($C_{1-4}$ alkoxy)-carbonyl, $C_1$–$C_4$ alkoxycarbonyloxy and methylenedioxy; naphtyl optionally carrying a substituent selected from the group consisting of hydroxy, $C_{1-4}$ alkoxy and $C_{1-4}$ acyloxy; furyl, thienyl or indolyl;

$R^2$ stands for hydrogen or $C_{1-4}$ alkyl;

$R^3$ and $R^4$ are independently $C_{1-4}$ alkoxy attached to positions 7 and 8 of the benzodiazepine ring, or $R^3$ and $R^4$ together form a 7,8-methylenedioxy group, and pharmaceutically acceptable acid addition salts thereof.

3. 1-[2-(Substituted vinyl)]-5H-2,3-benzodiazepine derivatives of formula (I) as defined in claim 1, wherein A and B together form a group of the formula =C=N— or =CH—NH—;

$R^1$ represents phenyl carrying a fluoro atom, a trifluoromethyl or a cyano group;

$R^2$ stands for hydrogen; and $R^3$ and $R^4$ together represent a 7,8- or 8,9-methylenedioxy group, and pharmaceutically acceptable acid addition salts thereof.

4. 1-[2-(Substituted vinyl)]-5H-2,3-benzodiazepine derivatives of formula (I) as claimed in claim 2, wherein A and B together form a =C=N— group;

$R^1$ represents phenyl optionally carrying one or two amino, di-($C_{1-3}$ alkyl)-amino or $C_{1-4}$ alkoxy substituent (s), $R^2$ stands for hydrogen and $R^3$ and $R^4$ together form 7,8-methylenedioxy, and pharmaceutically acceptable acid addition salts thereof.

5. The following compounds of formula (I) as defined in claim 1; 1-(4-dimethylaminostyryl)-4-methyl-7,8-dimethoxy-5H-2,3-benzodiazepine, 1-(4-aminostyryl) 4-methyl-7,8-dimethoxy-5H-2,3-benzodiazepine, 1-(3,4-dimethoxystyryl)-4-methyl-7,8-dimethoxy-5H-2,3-benzodiazepine, and pharmaceutically acceptable acid addition salts thereof.

6. 1-(4-Fluorostyryl)-4-methyl-7,8-methylenedioxy-5H-2,3-benzodiazepine, and pharmaceutically acceptable acid addition salts thereof.

7. A pharmaceutical composition comprising as active ingredient one or more compounds as claimed in claim 1 or a pharmaceutically acceptable acid addition salt thereof, in admixture with a suitable inert solid or liquid pharmaceutical carrier.

8. A pharmaceutical composition comprising as active ingredient one or more compounds as claimed in claim 2 or a pharmaceutically acceptable acid addition salt thereof, in admixture with a suitable inert solid or liquid pharmaceutical carrier.

9. A pharmaceutical composition comprising as active ingredient one or more compounds as claimed in claim 3 or a pharmaceutically acceptable acid addition salt thereof, in admixture with a suitable inert solid or liquid pharmaceutical carrier.

10. A pharmaceutical composition comprising as active ingredient a member selected from the group consisting of 1-(4-dimethylaminostyryl)-4-methyl-7,8-dimethoxy-5H-2,3-benzodiazepine, 1-(4-aminostyryl)-4-methyl-7,8-dimethoxy-5H-2,3-benzodiazepine, 1-(4-dimethoxystyryl)-4-methyl-7,8-dimethoxy-5H-2,3-benzodiazepine or pharmaceutically acceptable acid addition salts thereof and combinations thereof in admixture with a suitable inert solid or liquid carrier.

11. A pharmaceutical composition comprising as active ingredient 1-(4-fluorostyryl)-4-methyl-7,8-methylenedioxy-5H-2,3-benxodiazepine or a pharmaceutically acceptable acid addition salt thereof in admixture with a suitable inert solid or liquid carrier.

12. A method for the treatment of anxiety which comprises administering to a patient in need thereof an effective amount of a compound according to claim 1, or a pharmaceutically acceptable acid addition salt thereof.

* * * * *